(12) United States Patent
Innanje et al.

(10) Patent No.: US 11,734,333 B2
(45) Date of Patent: Aug. 22, 2023

(54) SYSTEMS AND METHODS FOR MANAGING MEDICAL DATA USING RELATIONSHIP BUILDING

(71) Applicant: SHANGHAI UNITED IMAGING INTELLIGENCE CO., LTD., Shanghai (CN)

(72) Inventors: Arun Innanje, Lexington, MA (US); Abhishek Sharma, Boston, MA (US); Terrence Chen, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 315 days.

(21) Appl. No.: 16/726,008

(22) Filed: Dec. 23, 2019

(65) Prior Publication Data

US 2021/0183496 A1 Jun. 17, 2021

Related U.S. Application Data

(60) Provisional application No. 62/949,035, filed on Dec. 17, 2019.

(51) Int. Cl.
*G06F 16/36* (2019.01)
(52) U.S. Cl.
CPC ................................ *G06F 16/367* (2019.01)
(58) Field of Classification Search
CPC ......... G06F 16/367; G06F 16/36; G06F 16/30
See application file for complete search history.

(56) References Cited

U.S. PATENT DOCUMENTS

| 7,636,702 | B2 * | 12/2009 | Perl | G06F 16/958 706/55 |
| 7,840,512 | B2 * | 11/2010 | Pandya | G16H 50/20 706/45 |
| 8,027,948 | B2 * | 9/2011 | Akkiraju | G06N 5/02 706/55 |
| 8,060,519 | B2 * | 11/2011 | Hosokawa | G06F 16/258 707/755 |
| 8,620,931 | B2 * | 12/2013 | Zillner | G06F 16/40 707/749 |
| 8,935,196 | B2 * | 1/2015 | Zillner | G06N 5/02 706/55 |
| 9,501,539 | B2 * | 11/2016 | Joshi | G06F 16/2471 |
| 2004/0193901 | A1 * | 9/2004 | Bharara | G16H 10/60 713/193 |

(Continued)

*Primary Examiner* — Miranda Le
(74) *Attorney, Agent, or Firm* — Faegre Drinker Biddle & Reath LLP (57) ABSTRACT

Methods and systems for organizing medical data. For example, a computer-implemented method includes receiving first data of a first data category, the first data having a first data format; extracting a first plurality of attributes from the first data using a first extractor; mapping the first plurality of attributes to an unified data format using a first mapper; receiving second data of a second data category, the second data having a second data format; extracting a second plurality of attributes from the second data using a second extractor; mapping the second plurality of attributes to the unified data format using a second mapper; and building an ontology for a use case by at least linking the first plurality of attributes and the second plurality of attributes.

16 Claims, 7 Drawing Sheets

(56) References Cited

U.S. PATENT DOCUMENTS

| | | | |
|---|---|---|---|
| 2006/0064328 A1* | 3/2006 | Datta | G06Q 10/06 705/2 |
| 2007/0064987 A1* | 3/2007 | Esham | G16H 30/20 382/128 |
| 2009/0103789 A1* | 4/2009 | Danner | G16H 30/20 382/128 |
| 2009/0124869 A1* | 5/2009 | Hu | A61B 5/369 600/301 |
| 2009/0132285 A1* | 5/2009 | Jakobovits | G06F 3/0482 705/3 |
| 2011/0087624 A1* | 4/2011 | Hale | G16H 70/00 706/11 |
| 2011/0093293 A1* | 4/2011 | G. N. | G16Z 99/00 707/E17.014 |
| 2013/0096947 A1* | 4/2013 | Shah | G16H 10/60 705/3 |
| 2013/0197938 A1* | 8/2013 | Bayouk | G16H 10/60 705/3 |
| 2014/0149407 A1* | 5/2014 | Qian | G06F 16/35 707/758 |
| 2014/0317080 A1* | 10/2014 | Piraino | G06F 16/9535 707/706 |
| 2016/0335403 A1* | 11/2016 | Mabotuwana | G16H 15/00 |
| 2017/0185674 A1* | 6/2017 | Tonkin | G06F 16/328 |
| 2019/0156921 A1* | 5/2019 | Kohli | G06N 20/00 |
| 2020/0279622 A1* | 9/2020 | Heywood | G16H 20/10 |

* cited by examiner

SYSTEMS AND METHODS FOR MANAGING MEDICAL DATA USING RELATIONSHIP BUILDING

1. CROSS-REFERENCES TO RELATED APPLICATIONS

This application claims priority to U.S. Patent Application No. 62/949,035 filed Dec. 17, 2019, which is incorporated by reference herein for all purposes.

2. BACKGROUND OF THE INVENTION

Certain embodiments of the present invention are directed to medical data management. More particularly, some embodiments of the invention provide methods and systems for managing medical data using relationship building. Merely by way of example, some embodiments of the invention are configured to manage radiology data and hospital data. But it would be recognized that the invention has a much broader range of applicability.

Currently, a large number of Hospitals uses PACS-based systems to store data, such as radiology data. PACS provides a relatively primitive query mechanism for a user to search for data, which has limited the ability of Radiologists and scientists to find the right data, such as for training purposes. Additionally, medical patients often have a wide variety of data types associated with them, saved in different locations and in different formats, making it difficult for a user to find the correct data of interest. Systems and methods with improved organization of medical data are desired, such as for better searching and data recalling.

3. BRIEF SUMMARY OF THE INVENTION

Certain embodiments of the present invention are directed to medical data management. More particularly, some embodiments of the invention provide methods and systems for managing medical data using relationship building. Merely by way of example, some embodiments of the invention are configured to manage radiology data and hospital data. But it would be recognized that the invention has a much broader range of applicability.

In various embodiments, a computer-implemented method for organizing medical data includes receiving first data of a first data category, the first data having a first data format; extracting a first plurality of attributes from the first data using a first extractor; mapping the first plurality of attributes to an unified data format using a first mapper; receiving second data of a second data category, the second data having a second data format; extracting a second plurality of attributes from the second data using a second extractor; mapping the second plurality of attributes to the unified data format using a second mapper; and building an ontology for a use case by at least linking the first plurality of attributes and the second plurality of attributes.

In various embodiments, a system for organizing medical data includes a first data receiving module configured to receive first data of a first data category, the first data having a first data format; a first attribute extracting module configured to extract a first plurality of attributes from the first data using a first extractor; a first attribute mapping module configured to map the first plurality of attributes to an unified data format using a first mapper; a second data receiving module configured to receive second data of a second data category, the second data having a second data format; a second attribute extracting module configured to extract a second plurality of attributes from the second data using a second extractor; a second attribute mapping module configured to map the second plurality of attributes to the unified data format using a second mapper; and an ontology building module configured to build an ontology for a use case by at least linking the first plurality of attributes and the second plurality of attributes.

In various embodiments, a non-transitory computer-readable medium with instructions stored thereon, that when executed by a processor, causes the processor to perform one or more processes including: receiving first data of a first data category, the first data having a first data format; extracting a first plurality of attributes from the first data using a first extractor; mapping the first plurality of attributes to an unified data format using a first mapper; receiving second data of a second data category, the second data having a second data format; extracting a second plurality of attributes from the second data using a second extractor; mapping the second plurality of attributes to the unified data format using a second mapper; and building an ontology for a use case by at least linking the first plurality of attributes and the second plurality of attributes.

Depending upon embodiment, one or more benefits may be achieved. These benefits and various additional objects, features and advantages of the present invention can be fully appreciated with reference to the detailed description and accompanying drawings that follow.

5. DETAILED DESCRIPTION OF THE INVENTION

Certain embodiments of the present invention are directed to medical data management. More particularly, some embodiments of the invention provide methods and systems for managing medical data using relationship building. Merely by way of example, some embodiments of the invention are configured to manage radiology data and hospital data. But it would be recognized that the invention has a much broader range of applicability.

Figure 1:
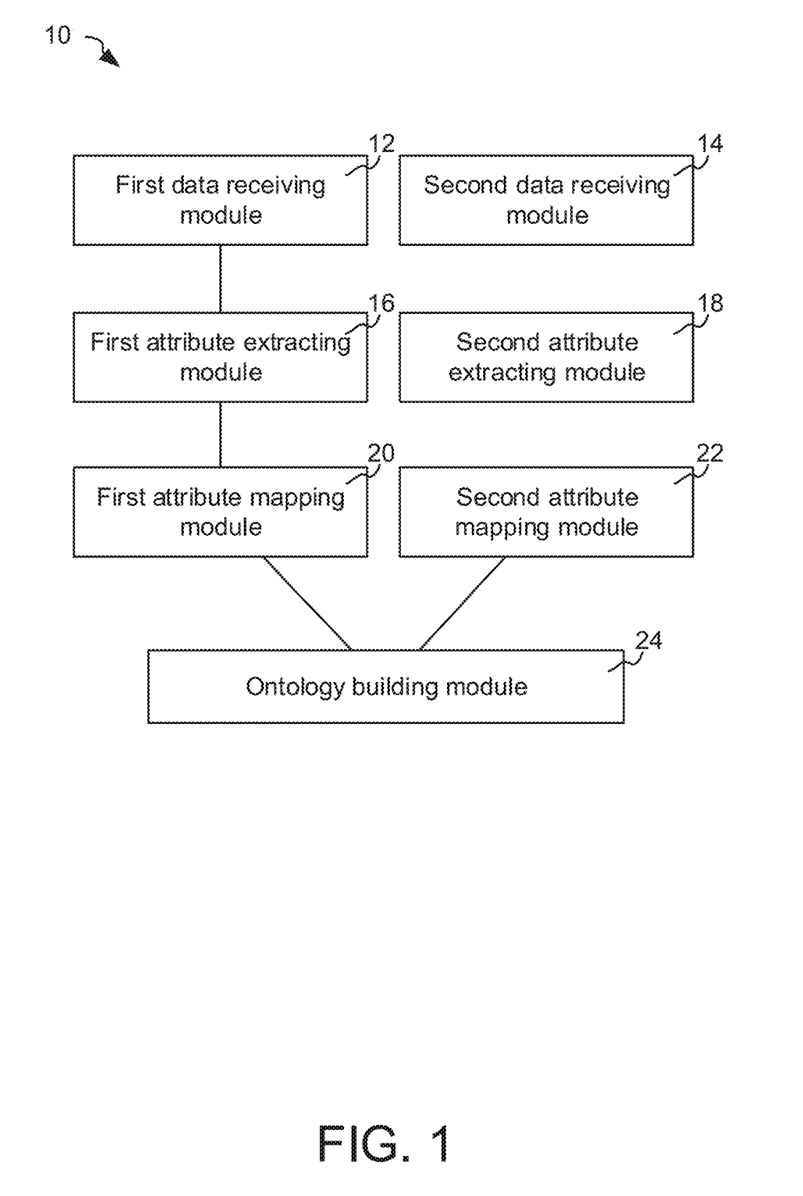
FIG. 1 is a simplified diagram showing a system for managing medical data, according to some embodiments.

FIG. 1 is a simplified diagram showing a system for managing medical data, according to some embodiments. This diagram is merely an example, which should not unduly limit the scope of the claims. One of ordinary skill in the art would recognize many variations, alternatives, and modifications. In some examples, the system 10 includes a first data receiving module 12, a second data receiving module 14, a first attribute extracting module 16, a second attribute extracting module 18, a first attribute mapping module 20, a second attribute mapping module 22, and an ontology building module 24. In certain examples, the system 10 is configured to implement method S100 of FIG. 2. Although the above has been shown using a selected group of components, there can be many alternatives, modifications, and variations. For example, some of the components may be expanded and/or combined. Some components may be removed. Other components may be inserted to those noted above. Depending upon the embodiment, the arrangement of components may be interchanged with others replaced.

In various embodiments, the first data receiving module 12 is configured to receive first data of a first data category. In certain examples, the first data having a first data format. In some examples, the first data category includes radiology data. In certain examples, the first data includes one of scan images and annotations. In certain examples, the scan images include CT images, MRI images, and/or PET images. In some examples, the first data receiving module 12 is further configured to receive the first data by a first computer of a medical computer network.

In various embodiments, the second data receiving module 14 is configured to receive second data of a second data category. In certain examples, the second data having a second data format. In some examples, the second data category includes profile data. In certain examples, the second data includes dietary habits, lifestyle habits, physical data, and/or genetic history. In various examples, the second data category includes clinical data. In certain examples, the second data includes electrocardiogram data, electroencephalogram data, and/or blood report data. In some examples, the second data category includes diagnostic data. In certain examples, the second data includes symptoms, diseases, conditions, and/or treatment plans. In certain examples, the second data receiving module 14 is further configured to receive the second data by a second computer of the computer network.

In various embodiments, the first attribute extracting module 16 is configured to extract a first plurality of attributes from the first data using a first extractor. In some examples, the first extractor is a machine learning model trained to extract attributes from data having the first data format. In some examples, the first attribute extracting module 16 is configured to extract the first plurality of attributes at the first computer.

In various embodiments, the second attribute extracting module 18 is configured to extract a second plurality of attributes from the second data using a second extractor. In some examples, the second extractor is a machine learning model trained to extract attributes from data having the second data format. In certain examples, the second attribute extracting module 18 is configured extract the second plurality of attributes at the second computer.

In various embodiments, the first attribute mapping module 20 is configured to map the first plurality of attributes to an unified data format using a first mapper. In some examples, the unified data format is DICOM. In some examples, the first attribute mapping module 20 is further configured to assign a unified data tag to each attribute of the first plurality of attributes. In certain examples, the first attribute mapping module is configured to map the first data at the first computer.

In various embodiments, the second attribute mapping module 22 is configured to map the second plurality of attributes to the unified data format using a second mapper. In some examples, the second attribute mapping module 22 is further configured to assign a unified data tag to each attribute of the second plurality of attributes. In some examples, the first mapper and the first extractor are part of a first plugin module. In certain examples, the second mapper and the second extractor are part of a second plugin module. In certain examples, the second attribute mapping module 22 is configured to map the second data at the second computer.

In various embodiments, the ontology building module 24 is configured to build an ontology for a use case by at least linking the first plurality of attributes and the second plurality of attributes.

In certain embodiments, the system 10 further includes a user input module configured to receive user input including one or more custom attribute relationships to be linked. In some embodiments, the system 10 further includes a graph builder (or alternatively, use the ontology building module to generate an ontology graph based at least in part on the ontology to provide visual guidance to a user. In some embodiments, the system 10 further includes a repository configured to store the ontology in a searchable, shareable, and/or editable format. In some examples, the stored ontology is searchable through natural language. In some embodiments, the system 10 further includes a sharing module configured to share the mapped first data and the mapped second data with the computer network such that the first computer receives the mapped second data and the second computer receives the mapped first data.

Figure 2:
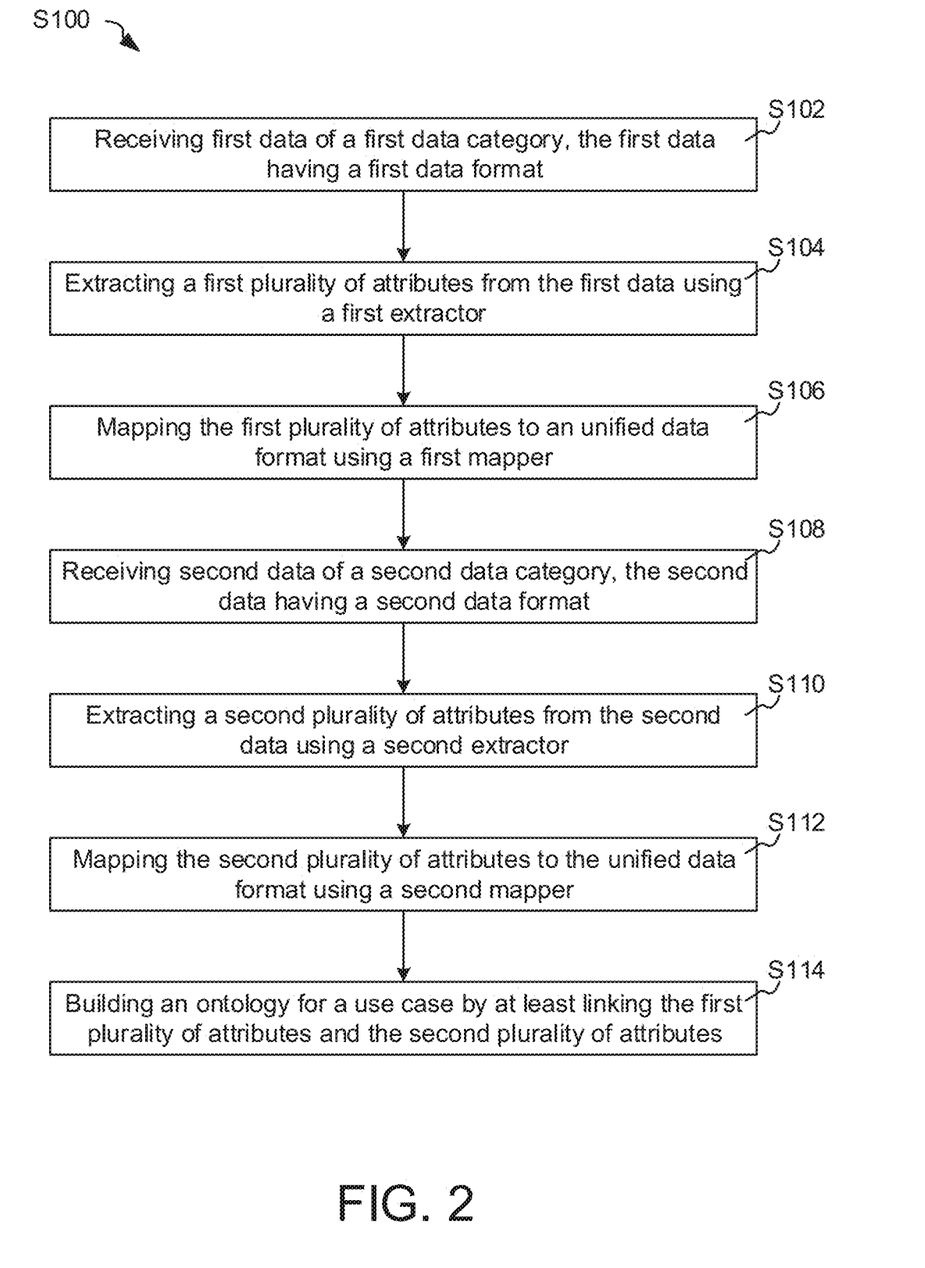
FIG. 2 is a simplified diagram showing a method for managing medical data, according to some embodiments.

FIG. 2 is a simplified diagram showing a method for managing medical data, according to some embodiments. This diagram is merely an example, which should not unduly limit the scope of the claims. One of ordinary skill in the art would recognize many variations, alternatives, and modifications. In certain examples, the method S100 is implemented by the system 10 of FIG. 1. In some examples, the method S100 includes a process S102 of receiving first data of a first data category, the first data having a first data format, a process S104 of extracting a first plurality of attributes from the first data using a first extractor, a process S106 of mapping the first plurality of attributes to an unified data format using a first mapper, a process S108 of receiving second data of a second data category, the second data having a second data format, a process S110 of extracting a second plurality of attributes from the second data using a second extractor, a process S112 of mapping the second plurality of attributes to the unified data format using a second mapper, and a process S114 of building an ontology for a use case by at least linking the first plurality of attributes and the second plurality of attributes. Although the above has been shown using a selected group of processes for the method, there can be many alternatives, modifications, and variations. For example, some of the processes may be expanded and/or combined. Other processes may be inserted to those noted above. Some processes may be removed. Depending upon the embodiment, the sequence of processes may be interchanged with others replaced.

In various embodiments, the process S102 of receiving first data of a first data category, the first data having a first data format includes receiving the first data by a first computer of a medical computer network.

In various embodiments, the process S104 of extracting a first plurality of attributes from the first data using a first extractor includes extracting the first plurality of attributes at the first computer.

In various embodiments, the process S106 of mapping the first plurality of attributes to an unified data format using a first mapper includes assigning a unified data tag to each attribute of the first plurality of attributes. In some examples, mapping the first plurality of attributes includes mapping the first plurality of attributes at the first computer.

In various embodiments, the process S108 of receiving second data of a second data category, the second data having a second data format includes receiving the second data by a second computer of the computer network.

In various embodiments, the process S110 of extracting a second plurality of attributes from the second data using a second extractor includes extracting the second plurality of attributes at the second computer.

In various embodiments, the process S112 of mapping the second plurality of attributes to the unified data format using a second mapper includes assigning a unified data tag to each attribute of the second plurality of attributes. In some examples, mapping the second plurality of attributes includes mapping the second plurality of attributes at the second computer.

In various embodiments, the process S114 of building an ontology for a use case by at least linking the first plurality of attributes and the second plurality of attributes includes building an ontology for a cardiac patient.

In certain examples, the method S100 further includes receiving user input including one or more custom attribute relationships to be linked. In some examples, the receiving user input includes receiving user input via an interactive graphical interface. In some examples, the method S100 further includes generating an ontology graph based at least in part on the ontology to provide visual guidance to a user. In some examples, the method S100 further includes storing the ontology in a searchable, shareable, and/or editable format. In certain examples, the stored ontology is searchable through natural language. In certain examples, the method S100 further includes sharing the mapped first data and the mapped second data with the computer network such that the first computer receives the mapped second data and the second computer receives the mapped first data.

In some examples, the unified data format is DICOM. In some examples, the first data category includes radiology data. In certain examples, the first data includes one of scan images and annotations. In some examples, the scan images include CT images, MRI images, and/or PET images. In some examples, the second data category includes profile data. In certain examples, the second data includes dietary habits, lifestyle habits, physical data, and/or genetic history. In some examples, the second data category includes clinical data. In certain examples, the second data includes electrocardiogram data, electroencephalogram data, and/or blood report data. In some examples, the second data category includes diagnostic data. In certain examples, the second data includes symptoms, diseases, conditions, and/or treatment plans. In some examples, the first mapper and the first extractor are part of a first plugin module. In certain examples, the second mapper and the second extractor are part of a second plugin module. In some examples, the first extractor is a machine learning model trained to extract attributes from data having the first data format. In certain examples, the second extractor is a machine learning model trained to extract attributes from data having the second data format.

Figure 3:
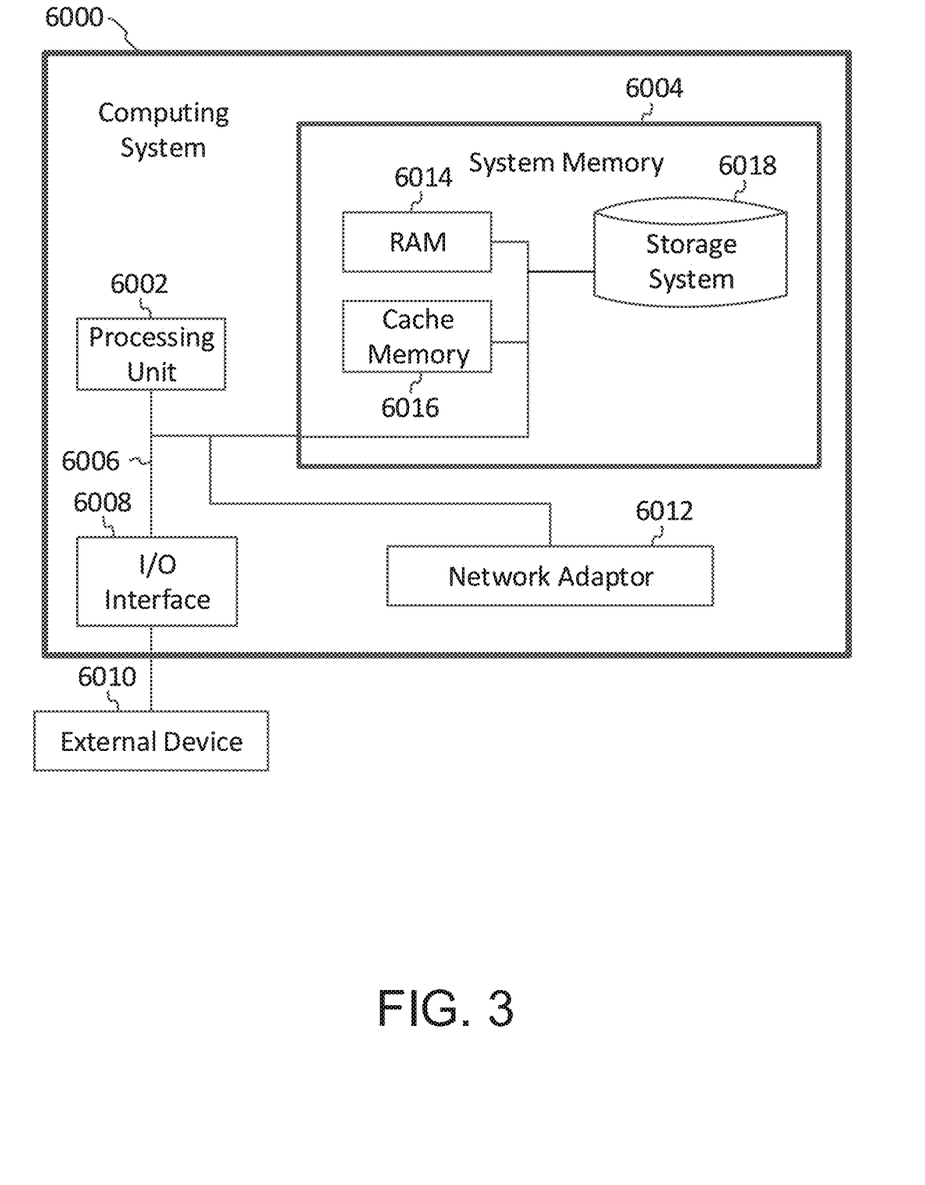
FIG. 3 is a simplified diagram showing a computing system, according to some embodiments.

FIG. 3 is a simplified diagram showing a computing system, according to some embodiments. This diagram is merely an example, which should not unduly limit the scope of the claims. One of ordinary skill in the art would recognize many variations, alternatives, and modifications. In certain examples, the computing system 6000 is a general-purpose computing device. In some examples, the computing system 6000 includes one or more processing units 6002 (e.g., one or more processors), one or more system memories 6004, one or more buses 6006, one or more input/output (I/O) interfaces 6008, and/or one or more network adapters 6012. In certain examples, the one or more buses 6006 connect various system components including, for example, the one or more system memories 6004, the one or more processing units 6002, the one or more input/output (I/O) interfaces 6008, and/or the one or more network adapters 6012. Although the above has been shown using a selected group of components for the computing system, there can be many alternatives, modifications, and variations. For example, some of the components may be expanded and/or combined. Other components may be inserted to those noted above. Some components may be removed. Depending upon the embodiment, the arrangement of components may be interchanged with others replaced.

In certain examples, the computing system 6000 is a computer (e.g., a server computer, a client computer), a smartphone, a tablet, or a wearable device. In some examples, some or all processes (e.g., steps) of the method S100 is performed by the computing system 6000. In certain examples, some or all processes (e.g., steps) of the method S100 is performed by the one or more processing units 6002 directed by one or more codes. For example, the one or more codes are stored in the one or more system memories 6004 (e.g., one or more non-transitory computer-readable media), and are readable by the computing system 6000 (e.g., readable by the one or more processing units 6002). In various examples, the one or more system memories 6004 include one or more computer-readable media in the form of volatile memory, such as a random-access memory (RAM) 6014, a cache memory 6016, and/or a storage system 6018 (e.g., a floppy disk, a CD-ROM, and/or a DVD-ROM).

In some examples, the one or more input/output (I/O) interfaces 6008 of the computing system 6000 is configured to be in communication with one or more external devices 6010 (e.g., a keyboard, a pointing device, and/or a display). In certain examples, the one or more network adapters 6012 of the computing system 6000 is configured to communicate with one or more networks (e.g., a local area network (LAN), a wide area network (WAN), and/or a public network (e.g., the Internet)). In various examples, additional hardware and/or software modules are utilized in connection with the computing system 6000, such as one or more micro-codes and/or one or more device drivers.

Figure 4:
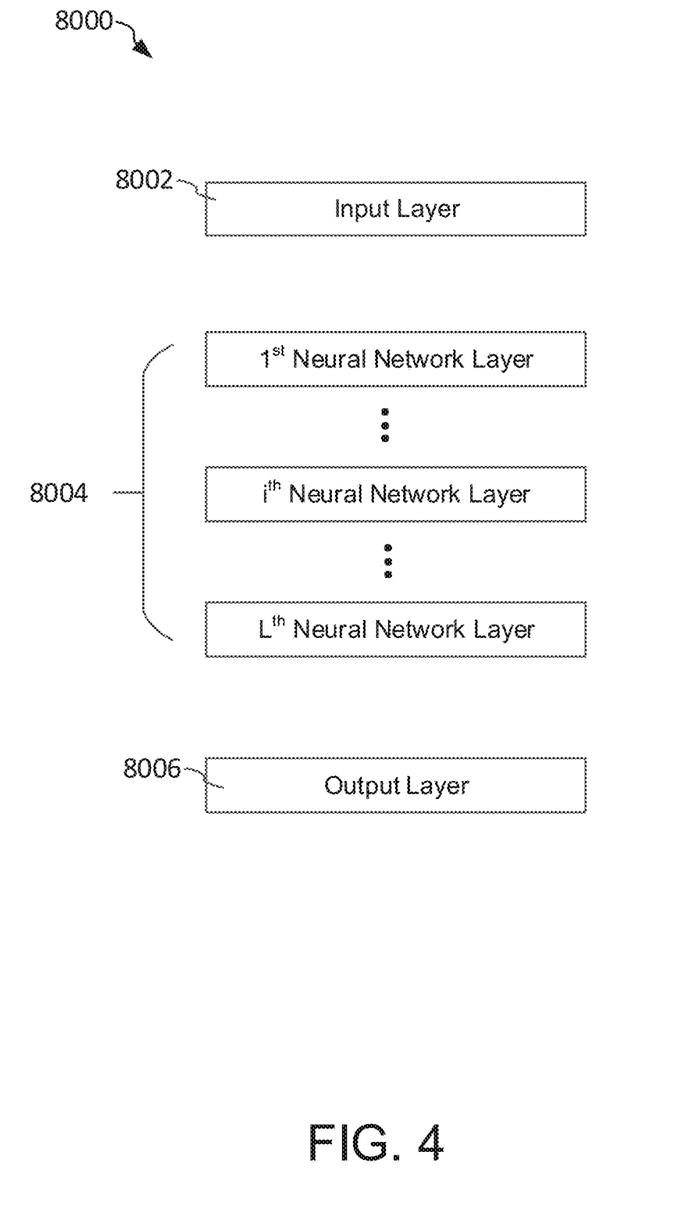
FIG. 4 is a simplified diagram showing a neural network, according to some embodiments.

FIG. 4 is a simplified diagram showing a neural network, according to certain embodiments. For example, the neural network is used by one or more of the machine learning models. This diagram is merely an example, which should not unduly limit the scope of the claims. One of ordinary skill in the art would recognize many variations, alternatives, and modifications. The neural network 8000 is an artificial neural network. In some examples, the neural network 8000 includes an input layer 8002, one or more hidden layers 8004, and an output layer 8006. For example, the one or more hidden layers 8004 includes L number of neural network layers, which include a $1^{st}$ neural network layer, ..., an $i^{th}$ neural network layer, ... and an $L^{th}$ neural network layer, where L is a positive integer and i is an integer that is larger than or equal to 1 and smaller than or equal to L. Although the above has been shown using a selected group of components for the neural network, there can be many alternatives, modifications, and variations. For example, some of the components may be expanded and/or combined. Other components may be inserted to those noted above. Some components may be removed. Depending upon the embodiment, the arrangement of components may be interchanged with others replaced.

In some examples, some or all processes (e.g., steps) of the method S100 is performed by the neural network 8000 (e.g., using the computing system 6000). In certain examples, some or all processes (e.g., steps) of the method S100 is performed by the one or more processing units 6002 directed by one or more codes that implement the neural network 8000. For example, the one or more codes for the neural network 8000 are stored in the one or more system memories 6004 (e.g., one or more non-transitory computer-readable media), and are readable by the computing system 6000 such as by the one or more processing units 6002.

In certain examples, the neural network 8000 is a deep neural network (e.g., a convolutional neural network). In some examples, each neural network layer of the one or more hidden layers 8004 includes multiple sublayers. As an example, the $i^{th}$ neural network layer includes a convolutional layer, an activation layer, and a pooling layer. For example, the convolutional layer is configured to perform feature extraction on an input (e.g., received by the input layer or from a previous neural network layer), the activation layer is configured to apply a nonlinear activation function (e.g., a ReLU function) to the output of the convolutional layer, and the pooling layer is configured to compress (e.g., to down-sample, such as by performing max pooling or average pooling) the output of the activation layer. As an example, the output layer 8006 includes one or more fully connected layers.

As discussed above and further emphasized here, FIG. 4 is merely an example, which should not unduly limit the scope of the claims. One of ordinary skill in the art would recognize many variations, alternatives, and modifications. For example, the neural network 8000 is replaced by an algorithm that is not an artificial neural network. As an example, the neural network 8000 is replaced by a machine learning model that is not an artificial neural network.

Figure 5:
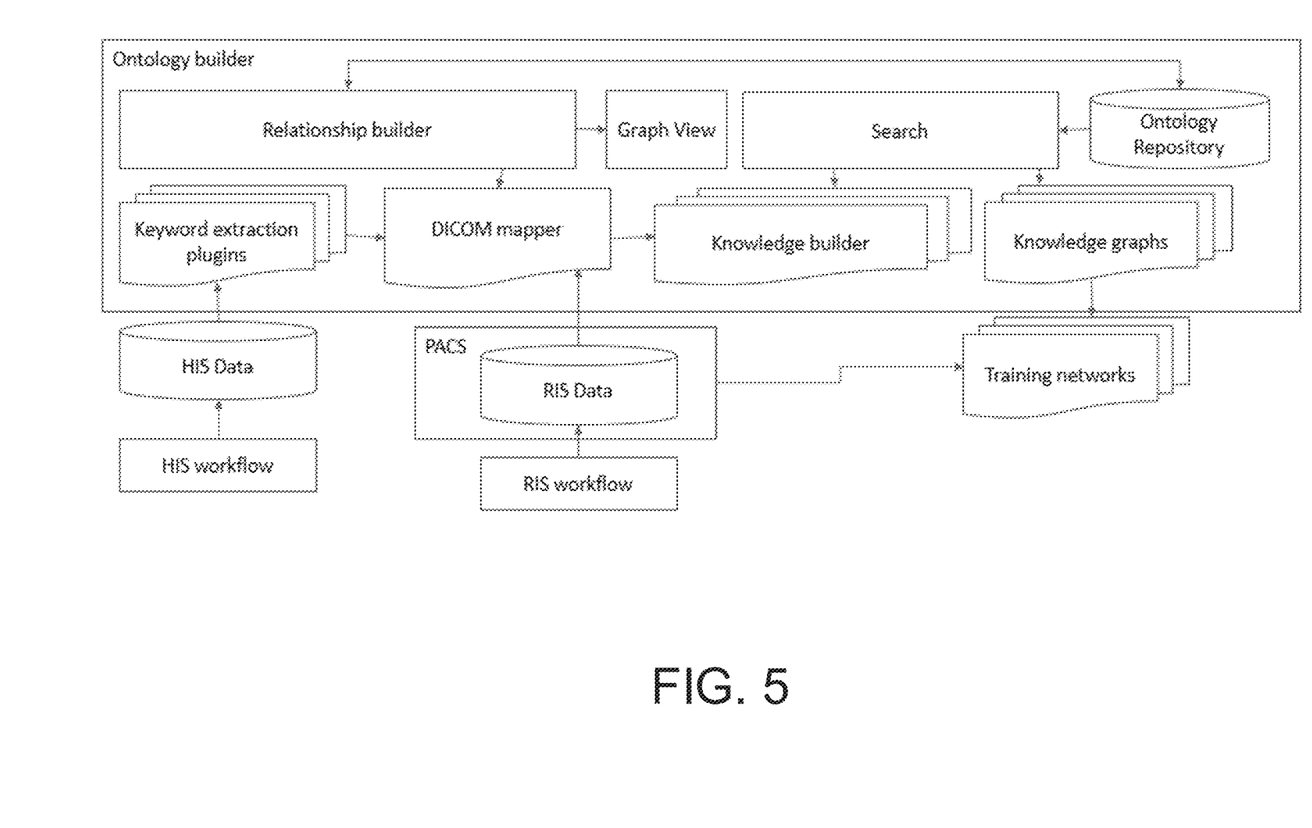
FIG. 5 is a simplified diagram showing an ontology builder system, according to some embodiments.

FIG. 5 is a simplified diagram showing an ontology builder system, according to some embodiments. In certain examples, the disclosed system is configured to receive Radiology Information System (RIS) data, such as Picture Archiving and Communication System (PACS) data and Hospital Information System (HIS) data. In certain examples, PACS and HIS data in a hospital may be used to build relationships in the ontology builder system. In certain examples, the disclosed system is an end to end system configured to allows bridging of Hospital information system and radiology information system (PACS), such as for building an ontology-based system around the radiology information system. In certain examples, the disclosed system is configured to provide data, such as via search, for a medical study (e.g., a novel medical study) and/or training an AI algorithm. In certain embodiments, the system of FIG. 5 includes a HIS data receiving module, a MS data receiving module, a knowledge extraction plugin, a DICOM mapper, a relationship builder, a graphical viewing module, a knowledge builder, an ontology repository, a search module, and an output module.

In certain embodiments, the HIS data receiving module is configured to receive HIS data, such as from a HIS workflow, such as to receive previously-collected HIS data from a database. In certain examples, HIS data and/or HIS workflow corresponds to patient registration, Physicians analysis, diagnostics, and/or treatment planning. In certain examples, HIS data are stored in one or more HIS formats (e.g., PDF).

In certain embodiments, the MS data receiving module is configured to receive RIS data, such as from a MS workflow, such as to receive previously-collected MS data from a database. In certain examples, MS data and/or MS workflow corresponds to scan images from a medical scanner (e.g., a CT, MR, or PET scanner). In certain examples, MS data are stored in one or more MS formats.

In certain embodiments, the knowledge extraction plugin is configured to extract data from HIS data, such as to extract data from various HIS data formats. In certain examples, the knowledge extraction plugin is further configured to transform HIS data into a unified data format mappable to one or more DICOM attributes. In certain embodiments, the knowledge extraction plugin is configured to extract data from RIS data, such as to extract data from various MS data formats. In certain examples, the knowledge extraction plugin is further configured to transform MS data into a unified data format mappable to one or more DICOM attributes.

In certain embodiments, the DICOM mapper (e.g., a mapper module) is configured to map, such as in accordance with the DICOM standard, one or more attributes (e.g., extracted from HIS and/or HIS data), to one or more DICOM keys and/or to convert data of heterogeneous data formats to the DICOM format.

In certain embodiments, the relationship builder is configured to build one or more relationships between a plurality of DCIOM attributes. In certain examples, the relationship builder is further configured to provide a graphics user interface (e.g., to a user) for inputting, linking, and/or designing the relationships.

In certain embodiments, the graphical viewing module is configured to, such as for complex attribute relationships, present visual verification, such as editable visualization (e.g., interactive graphs) for verification.

In certain embodiments, the knowledge builder is configured to receive mapped relationships, such as from the relationship builder. In certain examples, the knowledge builder is configured to build a knowledge graph (e.g., an ontology map), such as a final knowledge graph, such as based at least in part on the mapped relationships of the one or more attributes extracted from HIS data and MS data.

In certain embodiments, the ontology repository is configured to store one or more knowledge graphs, such as one or more ontology maps. In certain examples, the ontology repository is configured to store the one or more ontology maps in a searchable format, such as in a format that is recallable for modification of built relationships.

In certain embodiments, the search module is configured to provides a user interface for searching established knowledge graphs. In certain examples, the results of the search include one or more groups for target DICOM objects (e.g., related DICOM objects) that can be viewed and/or passed to a training network for training advanced networks (e.g., artificial neural networks).

In certain embodiments, the output module is configured to output the results of the search.

In certain embodiments, the disclosed system is configured to provide user an interactively ontology builder for HIS data and RIS data, such as for matting HIS attributes and/or RIS attributes to DICOM, such as to build knowledge graphs.

In certain examples, the disclosed system is configured to provide a mechanism for applying (e.g., uploading) one or more plugins configured for extracting and/or mapping unstructured data from HIS and/or RIS formats to DICOM format (e.g., standard format).

In certain examples, the disclosed system is configured to provide (e.g., to users) an ontology builder for DICOM data and/or provide a graph viewer for designing relationships, such as via manipulating relationship graphs.

In certain embodiments, the disclosed system is configured to build one or more knowledge graphs based on mapped attributes (e.g., extracted from HIS and/or MS data) and/or to provide searchable data based on the built one or more knowledge graphs.

In certain embodiments, the disclosed system is configured to enable one or more users to pull a knowledge graph including attribute relationships, such as a knowledge graph including to a related DICOM object, such as in a cluster.

In certain examples, the disclosed system is applicable for medical prognosis. For example, a user wanting to know the prevailing conditions (e.g., all conditions) that can lead to Glioblastoma may, through the system, apply a plugin configured to interpret (e.g., extract data information) one or more HIS records and/or to pick up key words related to patient symptoms and recommended one or more scans, and/or to further combine the findings with an ontology that has been built for patient, such as including one or more annotations, such as for reporting the identified relationships.

In certain embodiments, the disclosed system is configured to generate a knowledge graph, such as based on existing datasets in a hospital database. In certain examples, the system is configured for a user to run search queries in natural language, such as "what % patient having symptom a, b and c were diagnosed with glioblastoma grade 3 and how did the tumor react to treatment d?" In certain examples, the system is configured for a user to view the results of the search, which may include one or more images, annotations, and/or to pass on the data for training (e.g., training an artificial intelligence machine learning model) and/or advanced studies.

In certain embodiments, the disclosed system is configured to receive and/or process PACS data and/or RIS data, such as data stored in DICOM, which may have a strict semantics associated with thereby making data easily accessible. In certain examples, the disclosed system is configured to define one or more relationships between different types of data, such as based on the defined (e.g., extracted) DICOM attributes.

In certain embodiments, the disclosed system is configured to receive external queries, such as from an external query-system configured to utilize the one or more relationships built based on HIS data and/or RIS data, such as for allowing a user to build simply queries, such as in natural language. For example, the queries may be based on deterministic relationships such as "get all the patients diagnosed with grade 3 Glioblastoma." In certain examples, the system is configured to output the one or more established relationships, such as in the form of ontology graphs, such as for training.

In certain embodiments, the disclosed system is configured to receive medical data including scans from CT, MRI, etc. stored on PACS machines. For example, the medical data may include annotations and reports in a structured format (e.g., DICOM) and prepared by a radiologist, such as the result generated from performing diagnostics on RIS data. In certain examples, the medical data may include treatment plans such as suggestions of next steps for a treatment procedure and/or additional scans. In certain examples, the disclosed system is configured to, such as with the use of artificial intelligence (e.g., deep learning), support and aid a Radiologist's diagnostic procedures, such as for anomaly detection and/or decision making.

In certain embodiments, the disclosed system is configured to provide data relevant for training one or more deep learning networks.

In certain embodiments, the disclosed system is configured to provide one or more knowledge graphs, such as to help build ontologies based at least in part on well-structured data.

In certain embodiments, the disclosed system is configured for ontology-based search on PACS data, such as including design and workflow for augmenting user interaction with PACS-based systems and enabling the users to build complex queries around organized data and thereby allowing them to obtain deeper insights into the diseases being treated.

In certain examples, the disclosed system is configured for cardiac analysis. For example, the disclosed system is configured to aid diagnosis of a cardiac patient having patient data including dietary habits, physical data (e.g., weight, BMI), routines, habits, and/or a genetic history. In certain examples, the patient further has clinical data (e.g., ECG/EEG and/or blood reports) and/or radiology data (e.g., MR images and/or reports, and/or CT images and/or reports).

In certain examples, the disclosed system is configured to aid diagnosis of a plurality of patients having Cardiac issues, such as patients having a wide variety of data types. For example, the patients may have data stored in various systems and in various formats. In certain examples, the disclosed system is configured to consolidate (e.g., organize) patient data of various types (e.g., ones saved in various formats and/or in various locations) and to provide the data in a searchable manner in response to a user query (e.g., in natural language) such as "Does obese people smoking lead to increased cardiac strain?" "How likely people with Cardiac strain of 0.43 on segment 3 are likely related to a particular dietary or lifestyle?" and "Early diagnosis: Based on Lifestyle and ECG/blood report can we interpolate if the patient is likely to have a particular disease?" In certain examples, the disclosed system is configured to correlate the various patient data, including clinical diagnosis and radiology data.

Figure 6:
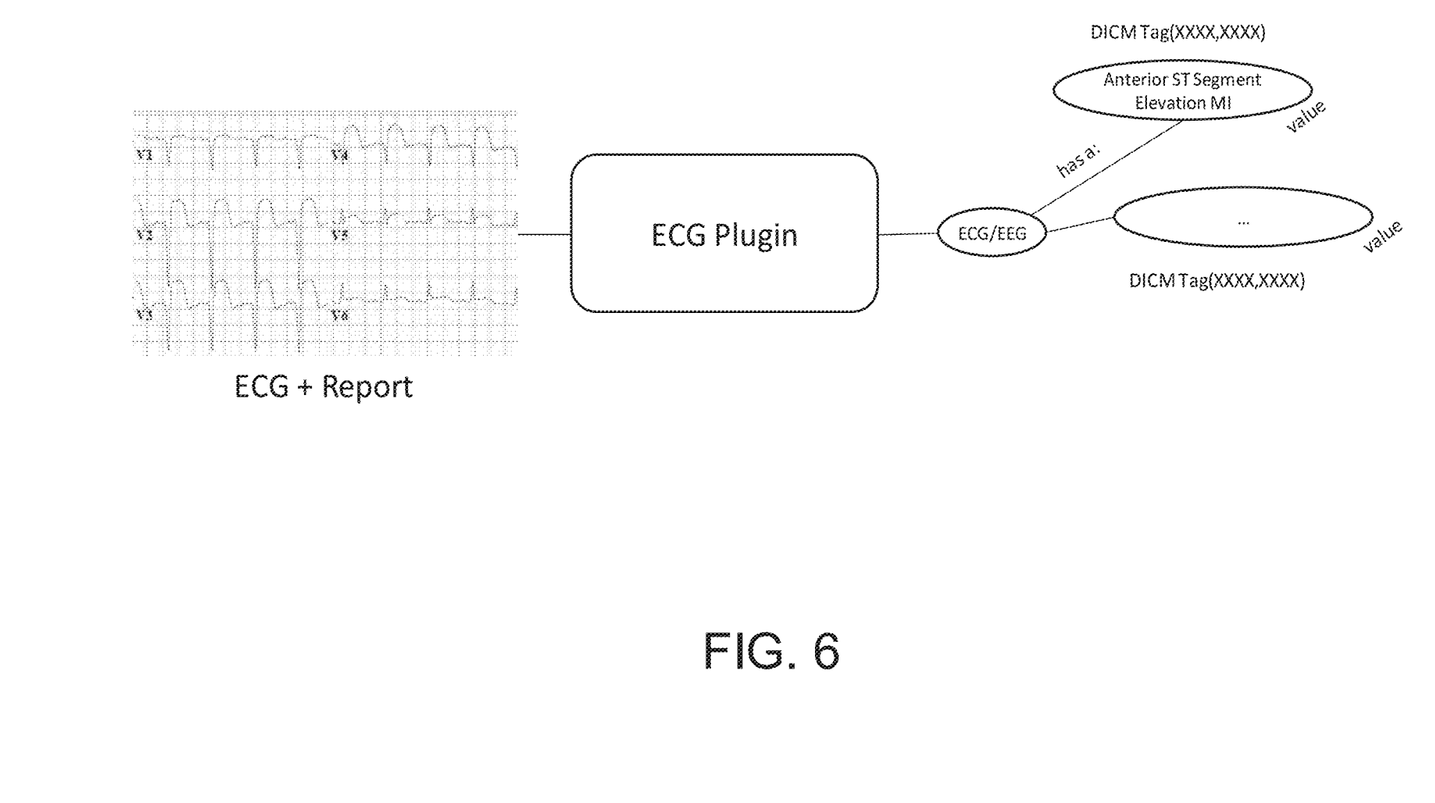
FIG. 6 is a simplified diagram showing the use of a ECG plugin, according to some embodiments.

FIG. 6 is a simplified diagram showing the use of a ECG plugin, according to some embodiments. In certain examples, for building ontology for a use case, the disclosed system is configured to link one or more ontology attributes to the DICOM standard. In certain examples, the disclosed system uses one or more plugins to extract information corresponding to a one or more subsets of data (e.g., data from HIS and RIS systems) into ontology attributes. For example, the ECG plugin in FIG. 6 shows a ECG plugin configured to receive ECG data and/or ECG report and output one or more DICOM attributes, which may correspond to one or more DICOM data tags.

Figure 7:
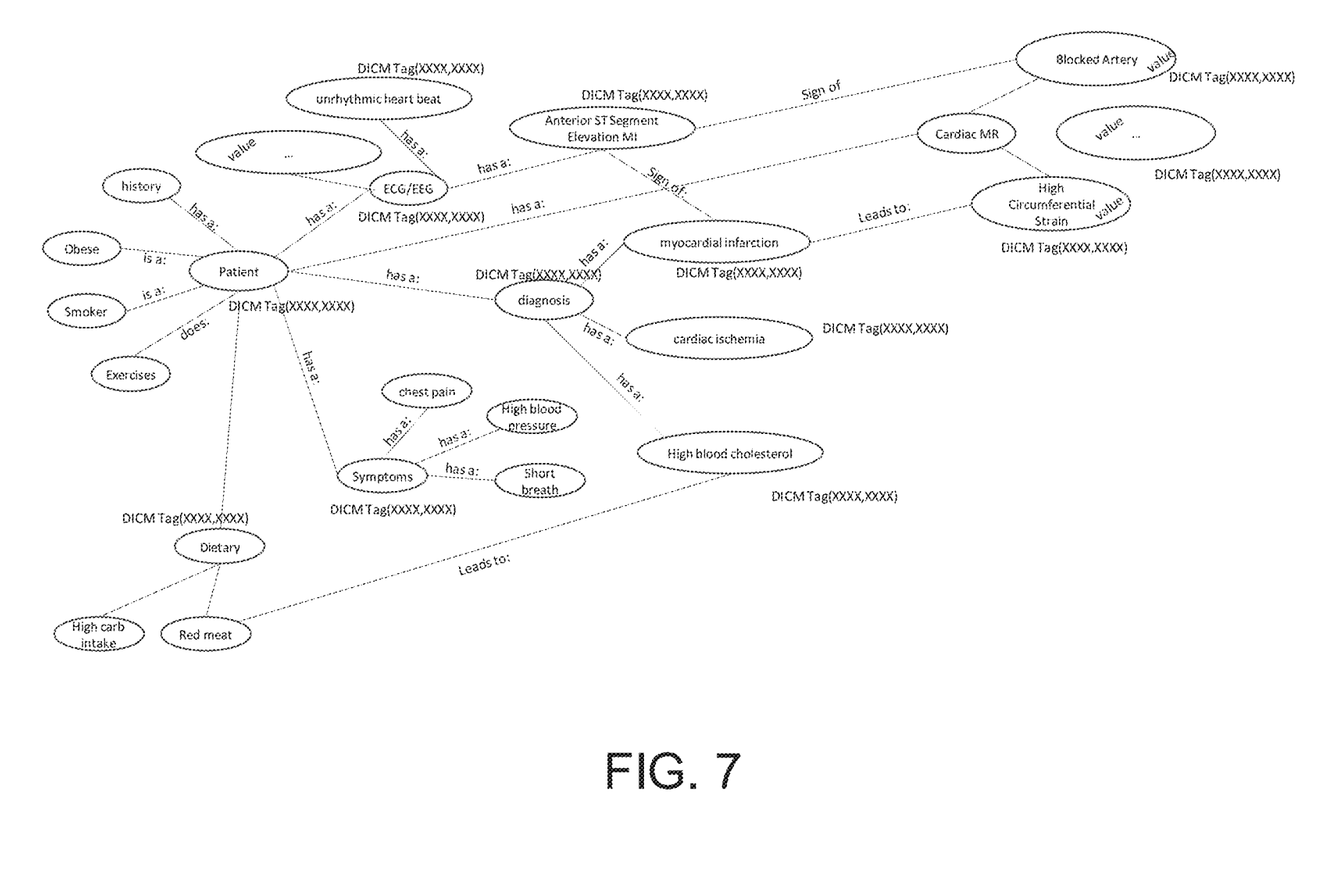
FIG. 7 is a simplified diagram showing an ontology builder, according to some embodiments.

FIG. 7 is a simplified diagram showing an ontology builder, according to some embodiments. In certain examples, the disclosed system is configured to combine data from various sources for building ontology relationships and/or ontology maps. In certain examples, the disclosed system is configured to allow relationships to be built, such as to be built between attributes extracted from various data (e.g., patient data, ECG data, diagnostic data, cardiac data). In certain examples, the disclosed system is configured to map clinical data to DICOM attributes and to bring uniformity in representation of data. In certain examples, the disclosed system is configured to map DICOM attributes to ontology. In certain examples, the disclosed system is configured to use one or more plugins to convert clinical data and diagnostic data to DICOM, such as for creating ontology relationships and/or ontology maps.

In various embodiments, a computer-implemented method for organizing medical data includes receiving first data of a first data category, the first data having a first data format; extracting a first plurality of attributes from the first data using a first extractor; mapping the first plurality of attributes to an unified data format using a first mapper; receiving second data of a second data category, the second data having a second data format; extracting a second plurality of attributes from the second data using a second extractor; mapping the second plurality of attributes to the unified data format using a second mapper; and building an ontology for a use case by at least linking the first plurality of attributes and the second plurality of attributes. In certain examples, the computer-implemented method is performed by one or more processors. In some examples, the computer-implemented method is implemented at least partly according to the method S100 of FIG. 2. In certain examples, the method is implemented at least partly by the system 10 of FIG. 1.

In some embodiments, the unified data format is DICOM.

In some embodiments, the mapping the first plurality of attributes to an unified data format using a first mapper includes assigning a unified data tag to each attribute of the first plurality of attributes. In certain examples, the mapping the second plurality of attributes to an unified data format using a second mapper includes assigning a unified data tag to each attribute of the second plurality of attributes.

In some embodiments, the first data category includes radiology data. In certain examples, the first data includes one of scan images and annotations.

In some embodiments, the scan images include CT images, MRI images, and/or PET images.

In some embodiments, the second data category includes profile data. In certain examples, the second data includes dietary habits, lifestyle habits, physical data, and/or genetic history.

In some embodiments, the second data category includes clinical data. In certain examples, the second data includes electrocardiogram data, electroencephalogram data, and/or blood report data.

In some embodiments, the second data category includes diagnostic data. In certain examples, the second data includes symptoms, diseases, conditions, and/or treatment plans.

In some embodiments, the first mapper and the first extractor are part of a first plugin module. In certain examples, the second mapper and the second extractor are part of a second plugin module.

In some embodiments, the first extractor is a machine learning model trained to extract attributes from data having the first data format. In certain examples, the second extractor is a machine learning model trained to extract attributes from data having the second data format.

In some embodiments, receiving user input including one or more custom attribute relationships to be linked.

In some embodiments, the receiving user input includes receiving user input via an interactive graphical interface.

In some embodiments, the method further includes generating an ontology graph based at least in part on the ontology to provide visual guidance to a user.

In some embodiments, the method further includes storing the ontology in a searchable, shareable, and/or editable format.

In some embodiments, the stored ontology is searchable through natural language.

In some embodiments, the receiving first data of a first data category includes receiving the first data by a first computer of a medical computer network. In certain examples, the receiving second data of a second data category includes receiving the second data by a second computer of the computer network.

In some embodiments, the extracting a first plurality of attributes includes extracting the first plurality of attributes at the first computer; the mapping the first plurality of attributes includes mapping the first plurality of attributes at the first computer; the extracting a second plurality of attributes includes extracting the second plurality of attributes at the second computer; and the mapping the second plurality of attributes includes mapping the second plurality of attributes at the second computer.

In some embodiments, the method further includes sharing the mapped first data and the mapped second data with the computer network such that the first computer receives the mapped second data and the second computer receives the mapped first data.

In various embodiments, a system for organizing medical data includes a first data receiving module configured to receive first data of a first data category, the first data having a first data format; a first attribute extracting module configured to extract a first plurality of attributes from the first data using a first extractor; a first attribute mapping module configured to map the first plurality of attributes to an unified data format using a first mapper; a second data receiving module configured to receive second data of a second data category, the second data having a second data format; a second attribute extracting module configured to extract a second plurality of attributes from the second data using a second extractor; a second attribute mapping module configured to map the second plurality of attributes to the unified data format using a second mapper; and an ontology building module configured to build an ontology for a use case by at least linking the first plurality of attributes and the second plurality of attributes. In some examples, the system is implemented at least partly according to the system 10 of FIG. 1. In certain examples, the system is configured to perform, at least partly, the method S100 of FIG. 2.

In some embodiments, the unified data format is DICOM.

In some embodiments, the first attribute mapping module is further configured to assign a unified data tag to each attribute of the first plurality of attributes. In certain examples, the second attribute mapping module is further configured to assign a unified data tag to each attribute of the second plurality of attributes.

In some embodiments, the first data category includes radiology data. In certain examples, the first data includes one of scan images and annotations.

In some embodiments, the scan images include CT images, MRI images, and/or PET images.

In some embodiments, the second data category includes profile data. In certain examples, the second data includes dietary habits, lifestyle habits, physical data, and/or genetic history.

In some embodiments, the second data category includes clinical data. In certain examples, the second data includes electrocardiogram data, electroencephalogram data, and/or blood report data.

In some embodiments, the second data category includes diagnostic data. In certain examples, the second data includes symptoms, diseases, conditions, and/or treatment plans.

In some embodiments, the first mapper and the first extractor are part of a first plugin module. In certain examples, the second mapper and the second extractor are part of a second plugin module.

In some embodiments, the first extractor is a machine learning model trained to extract attributes from data having the first data format. In certain examples, the second extractor is a machine learning model trained to extract attributes from data having the second data format.

In some embodiments, the system further includes a user input module configured to receive user input including one or more custom attribute relationships to be linked.

In some embodiments, the system further includes a graph builder (or alternatively, use the ontology building module to generate an ontology graph based at least in part on the ontology to provide visual guidance to a user.

In some embodiments, the system further includes a repository configured to store the ontology in a searchable, shareable, and/or editable format.

In some embodiments, the stored ontology is searchable through natural language.

In some embodiments, the first data receiving module is further configured to receive the first data by a first computer of a medical computer network. In certain examples, the second data receiving module is further configured to receive the second data by a second computer of the computer network.

In some embodiments, the first attribute extracting module is configured to extract the first plurality of attributes at the first computer. In certain examples, the first attribute mapping module is configured to map the first data at the first computer. In certain examples, the second attribute extracting module is configured to extract the second plurality of attributes at the second computer. In certain examples, the second attribute mapping module is configured to map the second data at the second computer.

In some embodiments, the system further includes a sharing module configured to share the mapped first data and the mapped second data with the computer network such that the first computer receives the mapped second data and the second computer receives the mapped first data.

In various embodiments, a non-transitory computer-readable medium with instructions stored thereon, that when executed by a processor, causes the processor to perform one or more processes including: receiving first data of a first data category, the first data having a first data format; extracting a first plurality of attributes from the first data using a first extractor; mapping the first plurality of attributes to an unified data format using a first mapper; receiving second data of a second data category, the second data having a second data format; extracting a second plurality of attributes from the second data using a second extractor; mapping the second plurality of attributes to the unified data format using a second mapper; and building an ontology for a use case by at least linking the first plurality of attributes and the second plurality of attributes. In some examples, the non-transitory computer-readable medium with instructions stored thereon is implemented according to the method S100 of FIG. 2. In certain examples, the non-transitory computer-readable medium with instructions stored thereon is configured to be implemented at least partly by the system 10 (e.g., a terminal) of FIG. 1.

In some embodiments, the unified data format is DICOM.

In some embodiments, the non-transitory computer-readable medium with instructions stored thereon, that when executed by a processor, causes the processor to perform one or more processes including: assigning a unified data tag to each attribute of the first plurality of attributes and/or assigning a unified data tag to each attribute of the second plurality of attributes.

In some embodiments, the first data category includes radiology data. In certain examples, the first data includes one of scan images and annotations.

In some embodiments, the scan images include CT images, MRI images, and/or PET images.

In some embodiments, the second data category includes profile data. In certain examples, the second data includes dietary habits, lifestyle habits, physical data, and/or genetic history.

In some embodiments, the second data category includes clinical data. In certain examples, the second data includes electrocardiogram data, electroencephalogram data, and/or blood report data.

In some embodiments, the second data category includes diagnostic data. In certain examples, the second data includes symptoms, diseases, conditions, and/or treatment plans.

In some embodiments, the first mapper and the first extractor are part of a first plugin module. In certain examples, the second mapper and the second extractor are part of a second plugin module.

In some embodiments, the first extractor is a machine learning model trained to extract attributes from data having the first data format. In certain examples, the second extractor is a machine learning model trained to extract attributes from data having the second data format.

In some embodiments, the non-transitory computer-readable medium with instructions stored thereon, that when executed by a processor, causes the processor to perform one or more processes including: receiving user input including one or more custom attribute relationships to be linked.

In some embodiments, the non-transitory computer-readable medium with instructions stored thereon, that when executed by a processor, causes the processor to perform one or more processes including: receiving user input via an interactive graphical interface.

In some embodiments, the non-transitory computer-readable medium with instructions stored thereon, that when executed by a processor, causes the processor to perform one or more processes including: generating an ontology graph based at least in part on the ontology to provide visual guidance to a user.

In some embodiments, the non-transitory computer-readable medium with instructions stored thereon, that when executed by a processor, causes the processor to perform one or more processes including: storing the ontology in a searchable, shareable, and/or editable format.

In some embodiments, the stored ontology is searchable through natural language.

In some embodiments, the non-transitory computer-readable medium with instructions stored thereon, that when executed by a processor, causes the processor to perform one or more processes including: receiving the first data by a first computer of a medical computer network and/or receiving the second data by a second computer of the computer network.

In some embodiments, the non-transitory computer-readable medium with instructions stored thereon, that when executed by a processor, causes the processor to perform one or more processes including: extracting the first plurality of attributes at the first computer; mapping the first plurality of attributes at the first computer; extracting the second plurality of attributes at the second computer; and mapping the second plurality of attributes at the second computer.

In some embodiments, the non-transitory computer-readable medium with instructions stored thereon, that when executed by a processor, causes the processor to perform one or more processes including: sharing the mapped first data and the mapped second data with the computer network such that the first computer receives the mapped second data and the second computer receives the mapped first data.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code including program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A computer-implemented method for organizing medical data, the method comprising:
   receiving first data of a first data category, the first data having a first data format;
   extracting a first plurality of attributes from the first data using a first extractor;
   mapping the first plurality of attributes to an unified data format using a first mapper by at least:
      assigning a DICOM data tag to each attribute of the first plurality of attributes;
      wherein the unified data format is DICOM;
      wherein the DICOM data tag is associated with DICOM;
   receiving second data of a second data category, the second data having a second data format;
   extracting a second plurality of attributes from the second data using a second extractor;
   mapping the second plurality of attributes to the unified data format using a second mapper by at least:
      assigning a DICOM data tag to each attribute of the second plurality of attributes;
      linking the first plurality of attributes and the second plurality of attributes based at least in part upon one or more DICOM data tags;
   generating an ontology including a plurality of ontology relationships specific for a use case based on the first plurality of attributes, the second plurality of attributes, and a link between at least one of the first plurality of attributes and at least one of the second plurality of attributes; and generating an ontology graph based at least in part on the ontology to provide visual guidance to a user;
wherein:
the first extractor is a machine learning model trained to extract attributes from data having the first data format; and
the second extractor is a machine learning model trained to extract attributes from data having the second data format.

2. The computer-implemented method of claim 1, wherein:
the first data category includes radiology data; and
the first data includes one of scan images and annotations.

3. The computer-implemented method of claim 2, wherein the scan images include one of CT images, MRI images, and PET images.

4. The computer-implemented method of claim 1, wherein:
the second data category includes profile data; and
the second data includes one of dietary habits, lifestyle habits, physical data, and genetic history.

5. The computer-implemented method of claim 1, wherein:
the second data category includes clinical data; and
the second data includes one of electrocardiogram data, electroencephalogram data, and blood report data.

6. The computer-implemented method of claim 1, wherein:
the second data category includes diagnostic data; and
the second data includes one of symptoms, diseases, conditions, and treatment plans.

7. The computer-implemented method of claim 1, wherein:
the first mapper and the first extractor are part of a first plugin module; and
the second mapper and the second extractor are part of a second plugin module.

8. The computer-implemented method of claim 1, further comprising:
receiving user input including one or more custom attribute relationships to be linked.

9. The computer-implemented method of claim 1, wherein the receiving user input includes receiving user input via an interactive graphical interface.

10. The computer-implemented method of claim 1, further includes storing the ontology in a searchable, shareable, and editable format.

11. The computer-implemented method of claim 10, wherein the stored ontology is searchable through natural language.

12. The computer-implemented method of claim 1, wherein:
the receiving first data of a first data category includes receiving the first data by a first computer of a medical computer network; and
the receiving second data of a second data category includes receiving the second data by a second computer of the computer network.

13. The computer-implemented method of claim 12, wherein:
the extracting a first plurality of attributes includes extracting the first plurality of attributes at the first computer;
the mapping the first plurality of attributes includes mapping the first plurality of attributes at the first computer;
the extracting a second plurality of attributes includes extracting the second plurality of attributes at the second computer; and
the mapping the second plurality of attributes includes mapping the second plurality of attributes at the second computer.

14. The computer-implemented method of claim 13, further comprising:
sharing the mapped first data and the mapped second data with the computer network such that the first computer receives the mapped second data and the second computer receives the mapped first data.

15. A system for organizing medical data, the system comprising:
one or more processors;
a first data receiving module implemented by one or more processors to receive first data of a first data category, the first data having a first data format;
a first attribute extracting module implemented by the one or more processors to extract a first plurality of attributes from the first data using a first extractor;
a first attribute mapping module implemented by the one or more processors to map the first plurality of attributes to an unified data format using a first mapper by at least:
assigning a DICOM data tag to each attribute of the first plurality of attributes;
wherein the unified data format is DICOM;
wherein the DICOM data tag is associated with DICOM;
a second data receiving module implemented by the one or more processors to receive second data of a second data category, the second data having a second data format;
a second attribute extracting module implemented by the one or more processors to extract a second plurality of attributes from the second data using a second extractor;
a second attribute mapping module implemented by the one or more processors to map the second plurality of attributes to the unified data format using a second mapper by at least:
assigning a DICOM data tag to each attribute of the second plurality of attributes; and
an ontology building module implemented by the one or more processors to:
link the first plurality of attributes and the second plurality of attributes based at least in part upon one or more DICOM data tags;
generate an ontology including a plurality of ontology relationships specific for a use case based on the first plurality of attributes, the second plurality of attributes, and a link between at least one of the first plurality of attributes and at least one of the second plurality of attributes; and
generate an ontology graph based at least in part on the ontology to provide visual guidance to a user;
wherein:
the first extractor is a machine learning model trained to extract attributes from data having the first data format; and
the second extractor is a machine learning model trained to extract attributes from data having the second data format.

16. A non-transitory computer-readable medium with instructions stored thereon, that when executed by a processor, causes the processor to perform the processes including:

receiving first data of a first data category, the first data having a first data format;
extracting a first plurality of attributes from the first data using a first extractor;
mapping the first plurality of attributes to an unified data format using a first mapper by at least:
    assigning a DICOM data tag to each attribute of the first plurality of attributes;
    wherein the unified data format is DICOM;
    wherein the DICOM data tag is associated with DICOM;
receiving second data of a second data category, the second data having a second data format;
extracting a second plurality of attributes from the second data using a second extractor;
mapping the second plurality of attributes to the unified data format using a second mapper by at least:
    assigning a DICOM data tag to each attribute of the second plurality of attributes;
    linking the first plurality of attributes and the second plurality of attributes based at least in part upon one or more DICOM data tags;
generating an ontology including a plurality of ontology relationships specific for a use case based on the first plurality of attributes, the second plurality of attributes, and a link between at least one of the first plurality of attributes and at least one of the second plurality of attributes; and
generating an ontology graph based at least in part on the ontology to provide visual guidance to a user;
wherein:
    the first extractor is a machine learning model trained to extract attributes from data having the first data format; and
    the second extractor is a machine learning model trained to extract attributes from data having the second data format.

* * * * *